United States Patent [19]
Sullenger et al.

[11] Patent Number: 5,854,038
[45] Date of Patent: Dec. 29, 1998

[54] LOCALIZATION OF A THERAPEUTIC AGENT IN A CELL IN VITRO

[75] Inventors: Bruce Alan Sullenger, Westminster; Thomas Robert Cech, Boulder, both of Colo.

[73] Assignee: University Research Corporation, Boulder, Colo.

[21] Appl. No.: 324,362

[22] Filed: Oct. 14, 1994

Related U.S. Application Data

[63] Continuation of Ser. No. 77,745, Jan. 22, 1993, abandoned.

[51] Int. Cl.$^6$ .......................... C12N 15/86; C12N 15/11; C12N 5/00; C12N 5/10
[52] U.S. Cl. .................................. 435/172.3; 435/320.1; 536/24.5
[58] Field of Search .............................. 435/172.3, 320.1; 536/24.5

[56] References Cited

FOREIGN PATENT DOCUMENTS

WO/8911539  11/1989  WIPO .
WO90/13641  11/1990  WIPO .
WO 91/19798  12/1991  WIPO .

OTHER PUBLICATIONS

M.I. Johnston et al. (1993) Science 260:1286–1293.
D. Cournoyer et al. (1993) Annu. Rev. Immunol. 11:297–329.
M.B. Feinberg et al. (1992) Aids Res. and Human Retrovir. 8(6):1013–1022.
B. Dropulić et al. (1992) J. Virol. 66(3):1432–1441.
J.O. Ojwang et al. (1992) Proc. Natl. Acad. Sci. USA 89:10802–10806.
J.A. Zaia et al. (1992) Annals of NY Acad. Sci. 660:95–106.
R. Tellier et al (1985) Nature 318:414.
M.C. Poznansky et al (1991) Int. Conf. Aids 7(2): p. 25 (Abstract No. W.A. 13).
M. Weerasinghe et al (1991) J. Virology 65(10):5531–5534.
Sarver et al., 247 *Science* 1222, 1990, "Ribozymes as Potential Anti–HIV–1 Therapeutic Agents".
Haseloff and Gerlach, 334 *Nature* 585, 1988, "Simple RNA Enzymes with New and Highly Specific Endoribonuclease Activation".
Sullenger et al., 63 *Cell* 601, 1990, "Overexpression of TAR Sequences Renders Cells Resistant to Human Immunodeficiency Virus Replication".
Sullenger et al., 10 *Molecular and Cellular Biology* 6512, 1990, "Expression of Chimeric tRNA–Driven Antisense Transcripts Renders NIH 3T3 Cells Highly Resistant to Moloney Murine Leukemia Virus Replication".
Izant et al., 1 *Antisense Research and Development* 371, 1991, "Chimeric Antisense RNAs".
Richardson et al., 67(7) Journal of Virology 3997–4005, 1993.

*Primary Examiner*—George C. Elliott
*Assistant Examiner*—Johnny F. Railey, III
*Attorney, Agent, or Firm*—Lyon & Lyon LLP

[57] ABSTRACT

Method for enhancing the effect of a viral therapeutic agent in a cell in vitro on the viral target by tethering a localization signal to the therapeutic agent so that the agent localizes with the viral target in a cellular or viral compartment of the cell.

13 Claims, 4 Drawing Sheets

A. RETROVIRAL VECTORS

1. B2A

2. N2A:HAMβS

B. FATES OF TRANSCRIBED B2A RNAS IN PACKING CELLS

C. COLOCALIZATION / INHIBITION STRATEGY

Hamβ1G

Coding Oligonucleotide Sequence for Hamβ1G and Hamβ1D (Boxed Nucleotide Deleted in Hamβ1D):

5' - CGT AGT GTC TGA TGA GTC CGT GAG GAC G̲A̲A ACG CGA TCG G - 3'

Hamβ1G Ribozyme Sequence

```
5' - CGU AGU GU    ACG CGA UCG G - 3'
             C   A
              U   A
             G     G
            A   A  [G]
             U G G-C
                 U-A
                 C-G
                 C-G
                 G   A
                 U   G
```

Target β1 Sequence with Hamβ1G Ribozyme

3' - GCA UCA CAC UGC GCU AGC C - 5'
                ↓

```
5' - CGU AGU GU    ACG CGA UCG G - 3'
             C   A
              U   A
             G     G
            A   A  [G]
             U G G-C
                 U-A
                 C-G
                 C-G
                 G   A
                 U   G
```

FIG. 2A

Hamβ2G

Coding Oligonucleotide Sequence for Hamβ2G:

5' - TTC CGC CAC TGA TGA GTC CGT GAG GAC GAA ACG CCA CTG C - 3'

Hamβ2G Ribozyme Sequence

```
5' - UUC CGC CA    ACG CCA CUG C - 3'
             C   A
              U   A
             G     G
            A   A  G
             U G G-C
                 U-A
                 C-G
                 C-G
                 G   A
                 U   G
```

Target β2 Sequence with Hamβ2G Ribozyme

3' - AAG GCG GUC UGC GGU GAC G - 5'
                ↓

```
5' - UUC CGC CA    ACG CCA CUG C - 3'
             C   A
              U   A
             G     G
            A   A  G
             U G G-C
                 U-A
                 C-G
                 C-G
                 G   A
                 U   G
```

FIG. 2B

LOCALIZATION OF A THERAPEUTIC AGENT IN A CELL IN VITRO

This application is a continuation of application Ser. No. 07/007,745, filed Jan. 22, 1993, now abandoned.

BACKGROUND OF THE INVENTION

This invention relates to methods and agents useful for treatment of viral and other diseases.

Therapeutic agents for treatment of viral infections or disease include antisense oligonucleotides, decoy nucleic acids, and ribozymes. Other agents include drugs, such as AZT for the treatment of AIDS (which is caused by infection with the HIV virus). Generally, these therapeutic agents are administered to an infected site in a patient, or caused to circulate through the vascular system of the patient.

Sullenger et al., 63 *Cell* 601, 1990 and 10 *Mol. Cell Biol.* 6512, 1990 describe inhibition of MoMLV or HIV replication by use of chimeric tRNA-encoding antisense and/or decoy templates. "The intracellular localization of the tRNA-TAR fusion transcripts was not determined; however, it was previously shown that unprocessed tRNA transcripts are generally not transported to the cytoplasm and remain confined to the nucleus. Since tat-TAR interactions take place in the nucleus, this may have also contributed to the observed inhibition of HIV replication in cells expressing the tRNA-TAR transcripts." [Citations omitted.]

Izant et al., 1 *Antisense Research and Development* 371, 1991, describe chimeric snRNP genes fused to an antisense CAT gene. The transcripts were found in the cytoplasm and nucleus when injected into oocytes. The authors believe the antisense snRNPs function primarily in the nucleus.

Gilboa and Sullenger, WO 90/13641 and Gilboa WO 89/11539 describe systems related to those discussed above. All of these references are hereby incorporated by reference herein.

SUMMARY OF THE INVENTION

Prior localization of inhibitory RNAs which may be left in or transported to the nucleus attempt to flood a large organelle, approximately 10 $\mu$M in diameter (Alberts et al., Molecular Biology of the Cell 16–17, Garland Publishing Inc. New York, N.Y. 1983) with either antisense or decoy RNA inhibitors. These strategies do not specifically localize such inhibitors with any specific mRNA and pre-mRNA target even though approximately $10^5$–$10^6$ different targets exist inside the nucleus (Alberts et al., Molecular Biology of the Cell 409, Garland Publishing Inc., New York, N.Y. 1983).

The present invention however, localizes an inhibitory RNA to a much smaller compartment, e.g., the core of a retroviral particle approximately 50 nM in diameter and $10^{-6}$ to $10^{-7}$ the volume of the nucleus, in which a single large RNA or DNA species, the viral genomic RNA or DNA, exists (Telch, RNA Tumor Viruses (ed. Weiss et al.) 25–208, Cold Spring, Harbor Press, Cold Spring, Harbor, N.Y. 1984). This million fold difference in localization specificity is achieved by targeting the therapeutic to a sorting pathway which distinguishes viral genomic RNAs and DNAs from the rest of the RNAs and DNAs in the cell.

In contrast, prior localization strategies targeted RNA therapeutics to general cellular sorting pathways which do not distinguish between a large number of different RNAs (in which the targeted RNA often only comprises fraction of a percent of the total pool of RNAs flowing down the targeted pathway.) Therefore, the present invention is unique in that it localizes therapeutics to pathways which are specific for their target: where, previous localization strategies attempted to flood general pathways in which millions of incorrect targets exist alongside the correct target, and thus do not employ localization signals which distinguish a correct target from the large number of incorrect targets in the cell.

Applicant has discovered that it is advantageous in treatment of disease, e.g., viral disease, to cause the therapeutic agent useful for treating that disease to be localized in a specific cellular or viral compartment in which the target component, e.g., RNA, is localized. Without such localization of the therapeutic agent, little or no effective treatment may be observed. In general, Applicant has determined that an appropriate localization signal must be tethered to the therapeutic agent to cause it to be precisely located within an intracellular or organismal (e.g., viral) location. Such localization signals identify a target uniquely, or distinguish the target from a majority of incorrect targets within a cell.

For example, RNA-based inhibitors of viral replication can be localized by use of a viral packaging signal, or other equivalent element, to place the inhibitory RNA in the same location as the target RNA. In addition, protein-based antiviral agents may be produced as protein-localization signal chimerics using standard procedures to form a protein-localization signal element which causes localization of the antiviral portion of the chimera to an appropriate compartment.

Thus, in a first aspect, the invention features a method for enhancing the effect of a viral therapeutic agent in vivo on the viral target of that agent. The method includes the step of causing the agent to be localized in vivo with its target. In a related aspect, the invention features a viral therapeutic agent which is adapted for localization with the viral target of the agent in vivo.

Those in the art will recognize that many methods can be used for modification of existing therapeutic agents such that they are caused to be localized in an appropriate compartment with a viral target. Examples of these methods follow but are not limiting in the invention. Thus, for example, RNA molecules (all of which are well known in the art) such as decoy RNAs, ribozymes, and antisense RNA or DNA molecules can be synthesized in vivo from DNA molecules (or formed in vitro) such that they are covalently bonded with a viral targeting agent, examples of which are provided below. These agents are termed "localization signals". Alternatively, proteinaceous or polypeptide agents can be produced from DNA or RNA within a cell in the form of a chimeric polypeptide or protein in which one portion of the polypeptide has an anti-viral effect, and the other portion causes localization of the polypeptide to an appropriate cellular or viral compartment. In addition, various therapeutic agents may be synthesized in vitro and administered in any one of many standard methods to cause the administered therapeutic agent to be targeted to an appropriate cellular compartment within a patient.

By "enhancing" the effect of a therapeutic agent in vivo is meant that a localization signal targets that agent to a specific site within a cell and thereby causes that agent to act more efficiently. Thus, a lower concentration of agent administered to a cell in vivo has an equal effect to a larger concentration of non-localized agent. Such increased efficiency of the targeted or localized agent can be measured by any standard procedure well-known to those of ordinary skill in the art. In general, the effect of the agent is enhanced by placing the agent in a closer proximity with the target, so that it may have its desired effect on that target. This may be achieved by causing the agent to be located in a small defined compartment with the target (e.g., within a viral particle), or to be located in the same space within a compartment, e.g., in a nucleus at the location of synthesis of the target.

Localization signals include any proteinaceous or nucleic acid component which naturally becomes localized in the desired compartment, for example, a viral packaging signal, or its equivalent. Localization signals can be identified by those in the art as those signals which cause the molecule to which they are attached to become localized in certain compartments, and can be readily discovered using standard methodology. These localization signals may be tethered to the therapeutic agent by any desired procedure, for example, by construction of a DNA template which produces both the localization signal and therapeutic agent RNA as part of the same RNA molecule, or by covalent or ionic bond formation between two moieties. All that is essential in the invention is that the inhibitory agent be able to have its inhibitory effect when localized in the target site, and that the localization signal be able to localize that therapeutic agent to that target site. Examples of useful localization signals and cell compartments include viral genomic packaging signals, for example, for RNA virus genomes, including, retroviruses (HIV, HTLV I & II, other human retroviruses, ALV, RSV, avian sarcoma virus and other chicken retroviruses, MoMLV and other Mouse retroviruses, FeLV and other feline retroviruses, and all other retroviral genomic RNA packaging signals). Also included are all other RNA viruses packaging signals; e.g., hepatitis B virus, and all DNA virus genomic packaging signals, e.g., HSV I, and adenovirus. Other viral nucleic acid sorting signals include HIV's Rev response element, and any other nucleic acid sequence which causes viral RNA or DNA to be sorted in some unique way, e.g., retroviral frame shifting during translation.

Yet other examples include any cellular RNA localization signal which causes RNAs containing the signal to be sorted into a pathway which does not contain large numbers of incorrect targets; viral protein localization/assembly signals: e.g., Rev or gag proteins, or any other protein-based signals which cause viral proteins to be sorted in some unique way; target specific cellular protein-based localization signals: e.g., formed by tethering therapeutics to proteins which will be specifically localized with correct targets inside the cell, e.g., chimeric transcription factor-RNAse proteins which will localize the RNAse specifically to the site of a targeted gene's expression. (e.g., a NFκB-RNAse chimeric protein to inhibit HIV gene expression); any RNA, DNA, or protein selected for its localization to a target specific site inside the cell or the body, e.g., an RNA which binds the transcription factor NFκB and will be localized to sites of HIV gene expression; and creation of small organic molecules which mimic specific targeting signals, e.g., an organic molecule which mimics the HIV packaging signal, and which can be used to deliver organic inhibitors to HIV packaging sites.

Increasing the concentration of a viral inhibitor at an intracellular site important for viral replication or assembly is a general way to increase the effectiveness of antiviral agents. The above-described colocalization strategy can make use of a viral packaging signal to colocalize RNA or protein with a target responsible for viral replication. In this way viral replication can be reduced or prevented. This method can be employed to enhance the effectiveness of many antiviral agents, including antisense RNA and decoy RNAs, by tethering them to an appropriate localization signal to sort them to the therapeutically important intracellular and viral location where the viral replication machinery is active.

For example, to improve ribozyme and other RNA-based inhibition of HIV replication, the HIV packaging signal and/or the rev response element (RRE) (Cullen et al., 58 *Cell* 423, 1989) can be placed adjacent an inhibitory RNA to colocalize it with an HIV RNA to be destroyed (Lee et al., 4 *New Biol.* 66, 1992).

The effectiveness of protein-based antivirals agents may also be improved by exploiting such viral macromolecule sorting pathways. For example, a chimeric rev-RNAse protein can be created which contains the protein elements essential for localization of rev to the RRE sequence of HIV. This will also localize the RNAse of the chimera to a required HIV transcript.

Such colocalization strategies are not limited to using naturally occurring localization signals. Antiviral agents can be targeted to virally important intracellular locations by use of artificially evolved RNAs and/or protein decoys (Szostak, 17 *TIBS* 89, 1992). These evolved molecules are selected to bind to a viral protein and may be used to colocalize a selected inhibitor with a viral target by tethering the inhibitor to such a decoy.

Localization of small antiviral molecules to appropriate intracellular sites increases their usefulness. For example, if AZT is targeted only to the intracellular compartment where HIV reverse-transcribes its genome, its effectiveness is greatly increased, and its side effects reduced or eliminated. The effectiveness of other, non-viral, drugs may also be enhanced by creating systems to target them to appropriate intracellular compartments, cell types, or organs where they may best perform their particular function.

In other aspects, the invention features methods for enhancing the effect of nucleic acid-based therapeutic agents in vivo by colocalizing them with their target using an appropriate localization signal.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIGS. 1A–D and 1B are diagrammatic representations, respectively of the retroviral vectors B2A and N2A:Hamβ; FIG. 1C is a diagrammatic representation of the fate of transcribed B2A RNAs in retroviral packaging cells; FIG. 1D is a diagrammatic representation of a colocalization/inhibition strategy of the present invention;

FIGS. 2A and 2B are diagrammatic representations of various hammerhead ribozyme motifs used in the present invention; including the coding oligonucleotide sequence for Hamβ1G and Hamβ1D (SEQ ID No. 1); Hamβ1G ribozyme sequence (SEQ ID No. 2); Targetβ1 sequence (SEQ ID No. 3) with Hamβ1G ribozyme (SEQ ID No. 2); coding oligonucleotide sequence for Hamβ2G (SEQ ID No. 4); Hamβ2G ribozyme sequence (SEQ ID No. 5); and Target β2 (SEQ ID No. 6) with Hamβ2G ribozyme (SEQ ID No. 5); and FIGS. 3 and 4 are histograms representing inhibition of a target viral genomic RNA (as shown by reduction in viral titre) by selected ribozymes in vivo, as a model for viral targeting by the method of the present invention.

THERAPEUTIC AGENT TARGETING

Several antiviral strategies which employ RNAs as inhibitors of viral replication have been postulated. They include the use of antisense RNA, decoy RNAs, and ribozymes as inhibitors (Sullenger et al., 10 *Mol. Cell. Biol.* 6512, 1990; Sullenger et al., 63 *Cell* 601, 1990; Sarver et al., 247 *Science* 1222, 1990). The ability to target ribozymes to specifically cleave viral RNAs in vitro has led to much speculation about their potential therapeutic value as antiviral agents in vivo (Cech, 260 *JAMA* 3030, 1988; and Rossi, 3 *Curr. Opin. Biotech.* 3, 1992). To successfully transfer a ribozyme's or other inhibitor's potential as an antiviral agent from test tubes to cells and organisms, the characteristics which distinguish these settings must be considered. The rate of a ribozyme mediated trans-cleavage reaction in vitro can nearly reach the rate at which RNA duplexes form in solution, because the RNA molecules are freely diffusing in solution in the test tube. In cells, in contrast, RNAs do not appear to freely diffuse. Rather they appear to be highly compartmentalized and actively sorted to specific cellular locations (Lawrence et al., 87 *Proc. Natl. Acad. Sci. USA* 5420, 1990). Such compartmentalization of viral RNAs in vivo may reduce their availability to ribozymes.

Applicant proposes a strategy which takes advantage of a cell's propensity to compartmentalize biological molecules in an ordered fashion and indeed to place two nucleic acid molecules in close proximity. By sorting inhibitors to the same locations within cells as their targets, the inhibitor's concentration at its required site of action can be increased. This in turn will increase the effectiveness of the inhibitor and, by allowing lower doses of inhibitor to be administered, reduce its side effects.

In a similar manner, inhibitors of other types of viral targets may have their effectiveness increased. Additionally, other types of agents may also be appropriately targeted. For example, agents which increase activity of cellular components which in turn provides an advantageous effect. Thus, any viral therapeutic agent can be localized or concentrated within an appropriate compartment, and its efficacy thereby enhanced. Similarly, other types of therapeutic agents can also be improved.

Those in the art will recognize that the example below is a non-limiting example of the invention, and merely illustrates the general application of the invention. The example shows that the packaging signal of a virus can be used to localize a ribozyme to a target viral RNA. The extraordinary results observed in this example are illustrative of the profound effect that use of the invention will have on drug therapies. As noted above, the applicability of the invention is not limited to any particular type of RNA, protein, or other type of therapeutic agent, nor to the use of viral localization signals, but rather can be broadly applied to localization of any desired therapeutic agent to any desired compartment within a cell. The only limitation may be in the determination of the compartment in which the therapeutic agent will have its maximal effect. It is desirable in this invention that the localization be as specific as possible so that the concentration of agent necessary for treatment of an individual can be maintained as low as possible.

EXAMPLE

In order to illustrate the claimed invention, an experimental system was developed to demonstrate that ribozyme mediated trans-cleavage of viral RNAs in vivo can be rendered efficacious by the colocalization of ribozyme with respect to its target RNA within a cell. This experimental system takes advantage of some properties of retroviral replication as well as several technical developments associated with retroviral vector-mediated gene transfer. Two types of retroviral vectors (FIG. 1A) were employed in this study. The retroviral vector B2A contains the lacZ gene (Markowitz et al., 62 *J. Virol.* 1120, 1988).

The lacZ-encoding transcripts were targeted for cleavage by two hammerhead ribozymes (Uhlenbeck, 328 *Nature* 596, 1987, and Haseloff and Gerlach, 334 *Nature* 585, 1988) and were thus used to report ribozyme-mediated inhibition. The retroviral vector N2A:Hamβ1G encodes the selectable marker neo$^R$ and a hammerhead ribozyme. The vector N2A:Hamβ2G is identical except for alterations in the sequence of the flanking arms of the hammerhead that target it to a different region of the lacZ coding sequence (FIGS. 2A and 2B).

These vectors were used to transfer and express ribozyme-containing RNAs in an ecotropic packaging cell line containing the B2A retroviral vector (E86/B2A) (Markowitz et al., 62 *J. Virol.* 1120, 1988). In E86/B2A cells, identical lacZ-encoding transcripts have two distinct fates (FIG. 1B). Some of the transcripts serve as mRNAs and are transported to the cytoplasm for translation. The abundance of these mRNAs can be assessed by measuring the level of β-galactosidase enzyme activity within the cells. Other transcripts serve as genomic RNAs for the replication of the retroviral vector and are packaged into viral particles budding from the surface of the packaging cells (FIG. 1B). The abundance of these genomic RNAs can be assessed by determining the titer of lacZ-encoding virus emerging from the packaging cells.

B2A-derived transcripts are encapsidated into the budding viral particles because they include the Moloney murine leukemia virus (MoMLV) packaging signal, ψ. This packaging process is mediated by the ability of the MoMLV encapsidation machinery, supplied by the packaging cells, to recognize ψ-containing transcripts and transport them to sites of viral budding (Mann et al., 33 *Cell* 153, 1983, Goff, *Retroviruses and Disease* (ed. Hanafusa, H. Pinter, A. & Pullman M.E.) 1–19 (Academic Press, Inc. 1989).

This MoMLV encapsidation machinery was utilized to colocalize transcripts containing the anti-lacZ hammerhead ribozyme with the transcripts encoding the lacZ target. In packaging cells containing both B2A and N2A:Hamβ, the B2A and N2A:Hamβ derived RNAs are both targeted for both translation and packaging (FIG. 1C). In such cells the B2A and N2A:Hamβ genomic RNA transcripts are colocalized to sites of viral budding at the surface of the packaging cells by the MoMLV encapsidation machinery. Because each retroviral particle contains two genomic RNAs, substrate- and ribozyme-containing genomes may be copackaged (FIG. 1C) (Varmus et al., *RNA Tumor Viruses* (ed. Weiss, R., Teich, N., Varmus, H. & Coffin, J.) 369–512 (Cold Spring Harbor Press, Cold Spring Harbor, N.Y. 1984 and Panganiban 241 *Science* 1064–1069 (1988). Therefore, if the hammerhead ribozymes are active and the target sequences are accessible on these genomic RNAs, colocalization will enhance the efficiency of cleavage, and the titer of lacZ-encoding virus emerging from these cells will be reduced.

In addition, the lacZ and Hamβ transcripts which will serve as mRNAs are unlikely to be colocalized because the two transcripts will be generated from proviruses integrated at distant sites on the cellular chromosomes (Lawrence et al., 87 *Proc. Natl. Acad. Sci. USA* 5420, 1990, Varmus et al., *RNA Tumor Viruses* (ed. Weiss, R., Teich, N., Varmus, H. &

Coffin, J.) 369–512 (Cold Spring Harbor Press, Cold Spring Harbor, N.Y. 1984). mRNAs are transported through different quadrants for translation determined by the nuclear location where they are transcribed (Raap et al., 197 *Exp. Cell Res.* 319, 1991). Therefore, if colocalization of ribozyme and substrate RNAs enhances trans-cleavage of a substrate RNA within a cell, β-galactosidase protein production should be reduced by a smaller amount than reduction of lacZ viral titer in these cells.

To illustrate this phenomenon, the N2A:Hamβ1G and N2A:Hamβ2G retroviral vectors were cloned by ligating oligonucleotides corresponding to two different hammerhead ribozymes into the polycloning site of the vector N2A (FIGS. 2A and 2B) (Hantzopoulos et al., 86 *Proc. Natl. Acad. Sci. USA* 3519, 1989. An inactive hammerhead sequence, Hamβ1D (FIG. 2A), was inserted into N2A to serve as a control for the importance of ribozyme activity in these experiments. Hamβ1D contains a single nucleotide deletion in the catalytic core of the hammerhead ribozyme (FIG. 2A). Such a mutation has been shown to nearly eliminate a hammerhead ribozyme's catalytic activity in vitro (Ruffner et al., 29 Biochem 10695, 1990).

The N2A:Hamβ1G, N2A:Hamβ2G, N2A:Hamβ1D, and parental N2A retroviral vectors were transfected into the amphotropic packaging cell line AM12 (Markowitz et al., 167 *Virology* 400, 1988). Transfected cells were selected by addition of G418 to the media, and resistant cells were pooled. Vector-containing viral supernatants were isolated from cells containing each construct, and were used to infect $10^4$ E86/B2A cells at a multiplicity of infection (MOI) of 10. Retroviral-mediated gene transfer was used to introduce the ribozyme-containing templates into the E86/B2A cells instead of transfection to avoid the potential problems of variable lacZ expression associated with clonal isolation of E86/B2A cell lines.

The transduced E86/B2A cells were expanded and analyzed for β-galactosidase activity present within the cells, and for $neo^R$ and lacZ viral titers emerging from the cells (FIG. 3). No significant reduction of β-gal activity was observed in cells containing the functional hammerhead vectors, N2A:Hamβ1G and N2A:Hamβ2G, as compared to cells containing a control vector, N2A or N2A:Hamβ1D. Similarly, no difference was seen in $neo^R$ viral titer emerging from the various vector-containing cells. However, lacZ viral titers from N2A:Hamβ1G and N2A:Hamβ2G-containing cells were reduced by 90–92% compared to control vector-containing cells (FIG. 3).

In the experiment described above, $10^4$ E86/B2A cells were infected at an MOI of 10, expanded, and assayed for reduction of lacZ viral titer and protein production. The cells were not selected with G418 to insure that all cells contain a retroviral vector containing a ribozyme. To determine if any of the 8–10% of the escaping virus is generated from cells lacking a ribozyme construct, N2A:Hamβ infected cells were selected with G418, and assayed for reduction of lacZ viral titer and protein production. The lacZ viral titer generated from the G418 selected E86/B2A cells containing N2A:Hamβ1G and N2A:Hamβ2G is reduced by 95–97% as compared to G418-selected cells containing a control vector. Once again, no reduction in β-gal activity is observed in these cells.

The last 3–5% of the lacZ virus which escapes inhibition may result at least in part from packaging of two lacZ genomes into one viral particle (FIG. 1C). If packaging of RNA genomes were totally random, then one would expect that approximately 1% of the viral particles would contain two lacZ genomes, because ribozyme-containing genomes are in a 10-fold excess to lacZ viral genomes in the cells.

These results provide evidence that colocalization of a ribozyme with its substrate within a cell is essential for efficient cleavage of that target RNA in vivo. Furthermore, the results indicate that such colocalization is rate limiting for ribozyme-mediated cleavage of targeted RNAs in vivo, and that to improve ribozyme-mediated inhibition of viral gene expression the rate which a ribozyme finds its substrate in vivo must be increased.

In a second experiment, $10^4$ E86/B2A cells were infected at various MOIs to determine how the relative ratio of ribozyme to substrate containing transcripts within a cell affects the level of inhibition of lacZ viral titer emerging from these cells. As expected, with N2A:Hamβ1G and N2A:Hamβ2G, the inhibition of lacZ viral titer decreases as the MOI is dropped from 10 to 2 to 0.4; in contrast, no significant change in lacZ titer occurs when control vectors are used to infect at these MOIs (FIG. 4). This illustrates that the inhibition of lacZ viral titer is directly related to the presence of the chimeric localization signal-viral inhibitor.

This example demonstrates clearly that a viral localization signal can be used to target an antiviral agent to provide almost 100% efficiency in viral killing. While the use of a packaging signal is illustrated, those in the art will recognize that other viral localization signals can be used. It is important only that the site of the agent and target be the same. In addition, while the example used a ribozyme agent, it is clear that any other RNA, DNA or other agent can equally well be localized and its efficiency enhanced.

There now follows an example of a method for construction of novel localization signals in the form of RNA. This example is also not limiting in the invention, and those in the art will recognize that such evolution can be performed with other chemicals, which can then be used in this invention. While these examples involve coexpression of two RNAs, those in the art will recognize that standard techniques can be used to bond other types of molecules together, e.g., AZT and an HIV localization signal.

RNA evolution

As noted above, it is possible to use RNAs that have been evolved to achieve different binding properties as localization signals. For example, RNA can be evolved in a test tube to recognize specifically a given protein which is localized in some particular fashion in the cell. Such RNAs can thus be used to specifically recognize or seek out particular cellular compartments, and can be used in the present invention as a localization signal as described above. Thus, the evolved RNA can be used to specifically target the cellular compartment to which the protein it binds is localized. In this way, the RNA can be used to increase the concentration of a killing or other agent at an appropriate cellular site. For example, an RNA can be selected in vitro which binds to the transcription factor NFκB. Specifically, a pool of RNAs can be incubated with the protein NFκB, and RNAs which bind the protein can be isolated and amplified and evolved in vitro via the polymerase chain reaction or other amplification reaction. This process is repeated until RNA is evolved which binds to the desired protein, NFκB. In an HIV infected cell, such evolved RNAs will bind NFκB and be localized to sites of HIV gene expression along with the transcription factor. Therefore, the RNA can be used to localize therapeutics (e.g., an anti-HIV ribozyme) to sites of HIV gene expression by tethering the therapeutic to the RNA based NFκB localization signal. Such evolved RNAs will also be particularly useful in targeting therapeutic to particular cell or tissues. For example, an RNA can be evolved to bind a receptor on liver cells. Tethering a therapeutic agent to such an RNA will target it to the liver.

These RNAs are particularly useful in targeting of particular cells or tissues. For example, an RNA can be evolved to bind a receptor on liver cells. Tethering a therapeutic agent to such an RNA will target it to the liver. Such RNAs can also be used to target therapeutics to specific cells. For example, in a type I diabetic, an autoreactive B-cell produces and expresses on its surface autoantibodies which recognize the Insulin receptor (Zhang and Roth, 88 *Proc. Natl. Acad. Sci. USA* 9858, 1991). RNAs can be evolved in vitro to bind to such antibodies. Specifically, a pool of RNAs can be incubated with the antibody, and RNAs binding the antibody can be immunoprecipitated. The precipitated RNAs are then further evolved in vitro by amplification procedures (for example, the polymerase chain reaction), and the process repeated until RNA is evolved which binds the desired antibody variable domain (Tsai et al., 89 *Proc. Natl. Acad. Sci. USA* 8864, 1992.) At the same time, a second RNA can be evolved which binds to a receptor on a natural killer cell, or some other effector cell. The two RNA binding domains can then be bonded or synthesized together to form a localization signal to the autoantibody expressing cell and a therapeutic agent which attracts killer cells to the autoreactive B-cell. In this way, the localization signal targets the specific antibody producing B-cells, and the therapeutic agent acts to ensure that natural killer cells will target such antibody producing B-cells, thereby producing a useful therapeutic agent. Thus, as this example illustrates, RNAs which encode receptor binding signals can be employed to localize therapeutic agents directly or indirectly, by recruiting other cells, etc., to cells which express a targeted receptor.

Use

The above-described system is useful not only for in vivo administration of therapeutic agents, but also in in vitro cell culture, where it is important to maintain viral-free cells. For example, a cell may be provided with DNA encoding a chimeric antisense RNA molecule bonded to a specific viral localization signal. Such a chimeric construct can be caused to be expressed from a promoter in any desired fashion such that the cell can be caused to kill or prevent replication of any virus entering that cell. In this way, viral infections in in vitro cell culture can be avoided. Such a construct can also be used in an in vivo situation where it is important to maintain an individual virus-free either as a prophylactic or therapeutic. Such DNA can be introduced by standard gene therapy techniques, or the RNA may be directly injected by electroporation into any desired site. Those in the art will recognize that other standard techniques can be used to introduce the chimeric agents of this invention.

Antiviral constructs can also be used in an in vivo situation where it is important to maintain an individual virus-free or reduce an individual's viral load. Inhibition of viral replication by such localized antiviral agents can be used as either a prophylactic or therapeutic. For example, standard gene therapy techniques can be employed to introduce a transcription unit into human lymphocytes or pre-lymphocytes which will result in the expression of an RNA encoding an anti-HIV ribozyme tethered to the HIV packaging signal. If cells containing the anti-HIV ribozymes are infected by HIV, the ribozymes will be localized to sites of HIV packaging and inhibit viral replication by cleaving the HIV genomic RNA. In this manner HIV spread can be reduced or inhibited in an individual. Genes, encoding other antiviral agents which have been engineered so that the expressed agent is tethered to an appropriate localization signal to enhance its effectiveness, can be transferred to an individual by standard gene therapy techniques (e.g., use of a retroviral or other viral vector) or by various physical transfer techniques (e.g., liposomes). Those in the art will recognize that other standard techniques can be used to introduce the chimeric agents of this invention.

Genes encoding the chimeric agents discussed in this invention can also be used to generate transgenic plants and animals which are resistant to viral infection or replication. For example, a transcription unit can be created which results in the expression of RNAs containing both a ribozyme designed to cleave Avian leukosis virus (ALV) RNAs and the ALV viral packaging signal. DNA encoding this transcription unit can be used to create a transgenic chicken by transferring such DNA into chicken germ line cells. In the transgenic chicken all cells would contain and express the chimeric anti-ALV transgene. Thus, if ALV infects the transgenic chicken, viral spread would be reduced or eliminated in the animal because chimeric anti-ALV ribozyme encoding transcripts will be colocalized with and cleave ALV genomic RNAs in the chicken's cells. In this manner the severity of viral caused diseases can be greatly reduced or eliminated or both transgenic plants and animals.

Administration

Selected agents, e.g., oligonucleotide or ribozymes can be administered prophylactically, or to patients suffering from a target disease, e.g., by exogenous delivery of the agent to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of oligonucleotides are also suitable.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing antigen binding site found on most snRNAs, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes and antisense oligonucleotides, like most small molecules, are taken up by cells, albeit slowly. To enhance cellular uptake, the ribozyme may be modified essentially at random, in ways which reduce its charge but maintain specific functional groups required for RNA cleavage activity. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. (See, Cech, *Curr. Op. Structural Biol.*, 1992) These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge thereby facilitating diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

A liposome formulation which can associate ribozymes with the surface of lymphocytes and macrophages is also useful. This will provide enhanced delivery to HSV-infected cells by taking advantage of the specificity of macrophage and lymphocyte immune recognition of infected cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration.

Intraperitoneal administration also leads to entry into the circulation with the molecular weight or size of the ribozyme-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

The chosen method of delivery will result in cytoplasmic accumulation in the afflicted cells and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

The invention is particularly useful for administration of ribozymes, antisense molecules and decoy RNAs, and as the example described above demonstrates, can be most advantageously used in the present invention. Particular diseases that may be treated in this manner include any disease which can be treated by such RNAs, for example, HSV, HBV, EBV, and HIV infection; as well as various carriers (where the target molecule is located in a known cellular compartment).

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO: 1:

CGTAGTGTCT GATGAGTCCG TGAGGACGAA ACGCGATCGG 40

( 2 ) INFORMATION FOR SEQ ID NO: 2:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO: 2:

CGUAGUGUCU GAUGAGUCCG UGAGGACGAA ACGCGAUCGG 40

( 2 ) INFORMATION FOR SEQ ID NO: 3:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO: 3:

CCGAUCGCGU CACACUACG 19

( 2 ) INFORMATION FOR SEQ ID NO: 4:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO: 4:

TTCCGCCACT GATGAGTCCG TGAGGACGAA ACGCCACTGC 40

( 2 ) INFORMATION FOR SEQ ID NO: 5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

UUCCGCCACU GAUGAGUCCG UGAGGACGAA ACGCCACUGC    40

( 2 ) INFORMATION FOR SEQ ID NO: 6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GCAGUGGCGU CUGGCGGAA    19

Other embodiments are within the following claims.

We claim:

1. A method for enhancing the effect of a viral therapeutic agent in a cell in vitro on the viral target of said agent, comprising the step of:
tethering a localization signal to said therapeutic agent wherein said localization signal causes said therapeutic agent to be localized with said viral target in a cellular or viral compartment of said cell.

2. The method of claim 1, wherein said agent is selected from the group consisting of an antisense oligonucleotide, a decoy oligonucleotide, and a ribozyme.

3. The method of claim 1, wherein said localization signal is selected from the group consisting of viral packaging signals.

4. The method of claim 1, wherein said localization signal comprises a nucleic acid component.

5. The method of claim 1, wherein said localization signal comprises a protein component.

6. A viral therapeutic agent comprising at least one localization signal able to localize said agent in the same cellular or viral compartment with a viral target of said therapeutic agent in a cell in vitro.

7. The therapeutic agent of claim 6, wherein said agent is selected from the group consisting of an antisense oligonucleotide, a decoy oligonucleotide and a ribozyme.

8. The therapeutic agent of claim 6, wherein said localization signal is selected from the group consisting of viral packaging signals.

9. A therapeutic agent comprising a localization signal, wherein said localization signal is capable of localizing said therapeutic agent in the same cellular compartment as the target molecule of said therapeutic agent in a cell in vitro.

10. The therapeutic agent of any one of claims 6 or 9, wherein said localization signal comprises a nucleic acid component.

11. The therapeutic agent of any one of claims 6 or 9, wherein said localization signal comprises a protein component.

12. An expression vector including nucleic acid encoding the therapeutic agent of claims 6 or 9 in a manner which allows expression of said therapeutic agent within a cell in vitro.

13. The vector of claim 12, wherein said vector is derived from a retrovirus.

* * * * *

(12) EX PARTE REEXAMINATION CERTIFICATE (6534th)
United States Patent
Sullenger et al.

(10) Number: US 5,854,038 C1
(45) Certificate Issued: Nov. 25, 2008

(54) LOCALIZATION OF A THERAPEUTIC AGENT IN A CELL IN VITRO

(75) Inventors: Bruce Alan Sullenger, Westminster, CO (US); Thomas Robert Cech, Boulder, CO (US)

(73) Assignee: University Research Corporation, Boulder, CO (US)

Reexamination Request:
No. 90/006,036, Jun. 11, 2001

Reexamination Certificate for:
Patent No.: 5,854,038
Issued: Dec. 29, 1998
Appl. No.: 08/324,362
Filed: Oct. 14, 1994

Related U.S. Application Data

(63) Continuation of application No. 08/007,745, filed on Jan. 22, 1993, now abandoned.

(51) Int. Cl.
*C12N 15/00* (2006.01)
*C12N 15/86* (2006.01)
*C12N 15/11* (2006.01)
*C12N 5/00* (2006.01)
*C12N 5/10* (2006.01)
*C07H 21/02* (2006.01)

(52) U.S. Cl. .................. 435/455; 536/23.1; 536/24.5; 435/320.1; 435/456; 435/458

(58) Field of Classification Search .................. None
See application file for complete search history.

(56) References Cited

U.S. PATENT DOCUMENTS 5,166,059 A * 11/1992 Pastan et al. ............... 435/69.7
6,107,062 A *  8/2000 Hu et al. .................. 435/91.41

OTHER PUBLICATIONS

Dropulic, B., et al., 1991, "Ribozyme mediated suppression of HIV expression in tissue culture", in *Abstracts of papers presented at the 1991 meeting on RNA Tumor Viruses*, May 21–26, Cold Spring Harbor Laboratory, Cold Spring Harbor, New York, Abstract 311.*

Dropulic, B., et al., 1992, "Functional characterization of a U5 ribozyme: intracellular suppression of human immunodeficiency virus type 1 expression", J. Virol. 66(3):1432–1441.*

Natsoulis, G., and J.D. Boeke, 1991, "New antiviral strategy using capsid–nuclease fusion proteins", Nature 352(Aug. 15, 1991):632–635.*

* cited by examiner

*Primary Examiner*—Jeffrey S. Parkin

(57) ABSTRACT

Method for enhancing the effect of a viral therapeutic agent in a cell in vitro on the viral target by tethering a localization signal to the therapeutic agent so that the agent localizes with the viral target in a cellular or viral compartment of the cell.

US 5,854,038 C1

EX PARTE REEXAMINATION CERTIFICATE ISSUED UNDER 35 U.S.C. 307

Figure 1A:
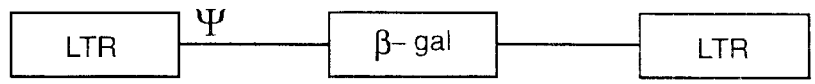
Figure 1B:
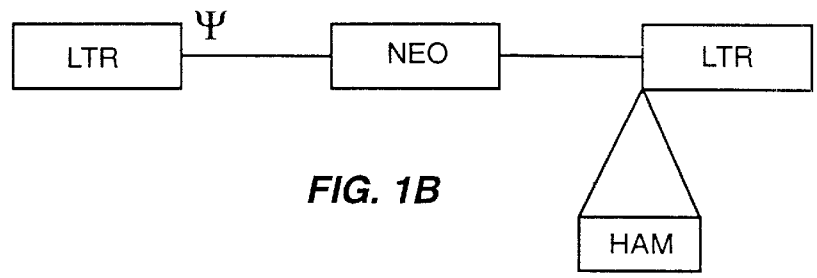
Figure 1C:
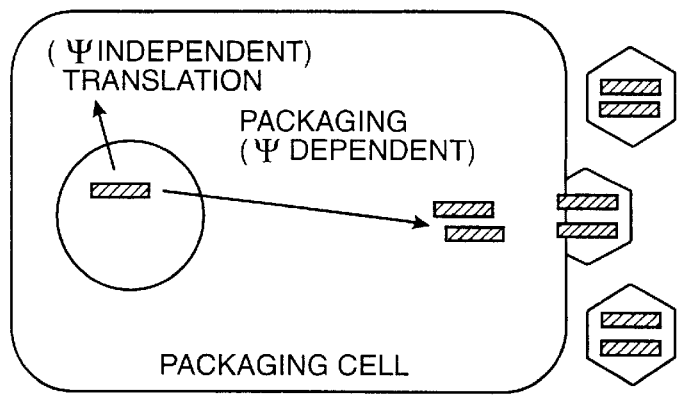
Figure 1D:
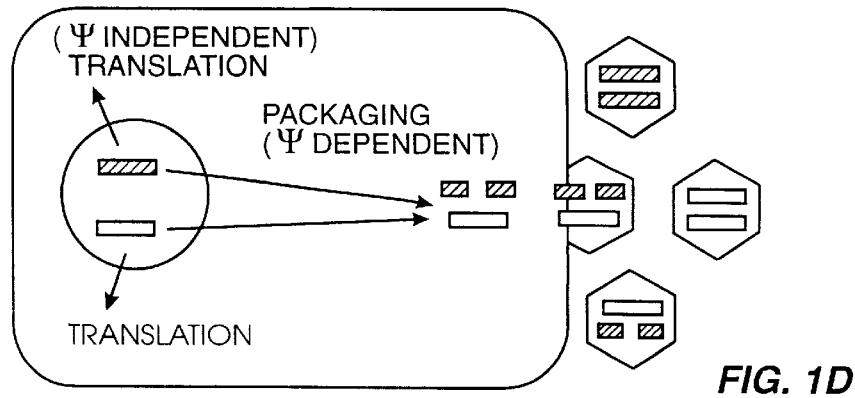
Figure 3:
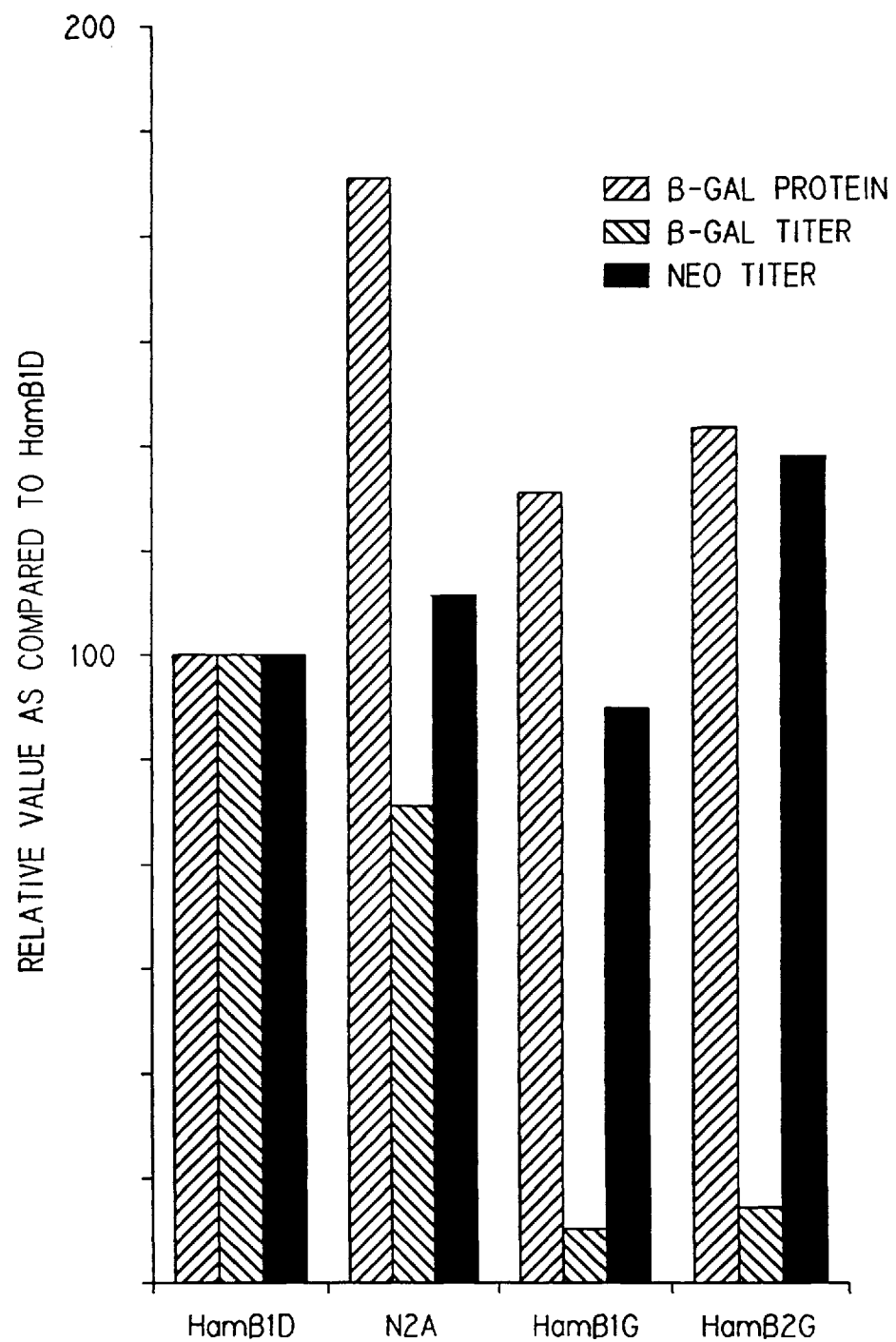
Figure 4:
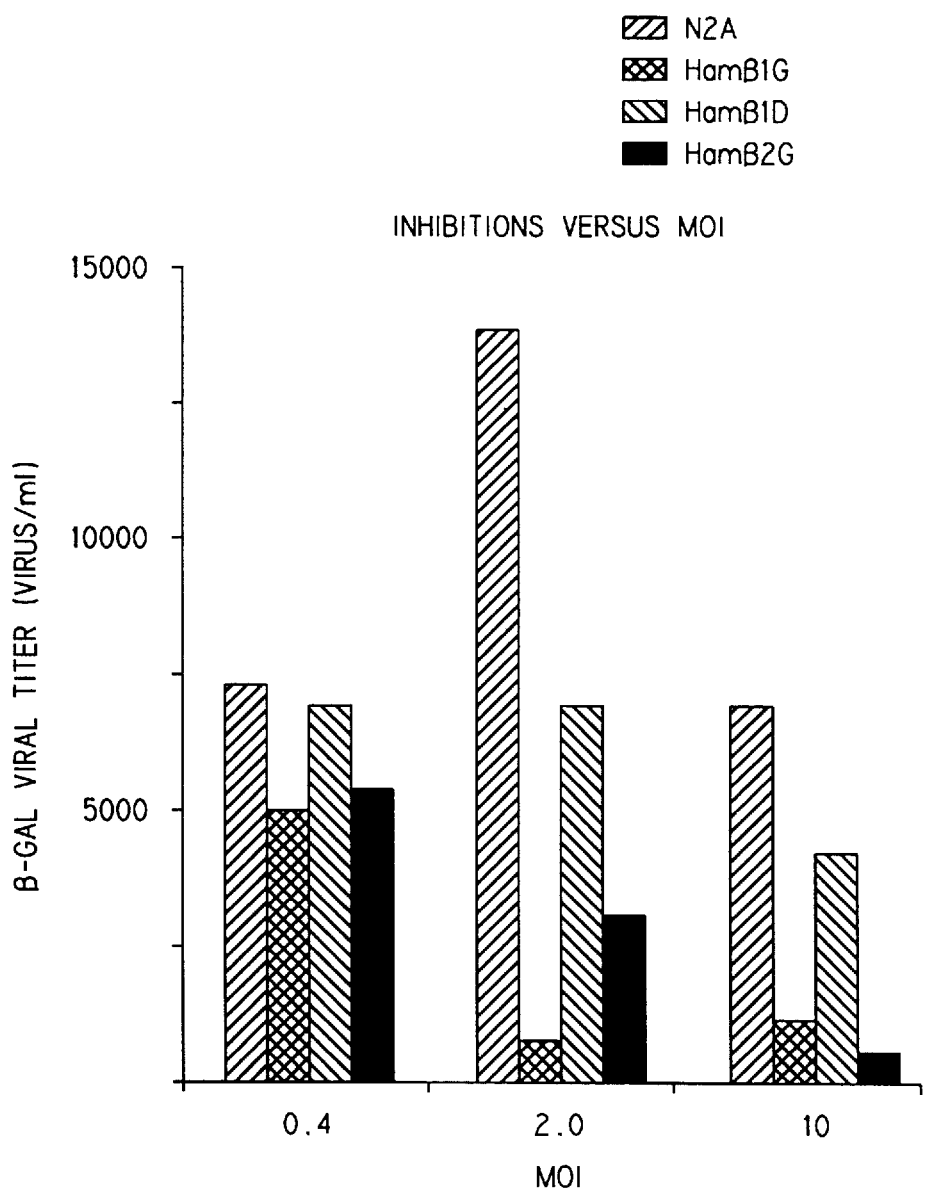

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4, 8 and 10–13 are cancelled.

Claims 5–7 and 9 are determined to be patentable as amended.

New claims 14–29 are added and determined to be patentable.

5. [The ] *A* method [of claim 1, wherein said localization signal comprises a protein component] *for enhancing the effect of a viral therapeutic agent in a cell in vitro on the viral target of said viral therapeutic agent, wherein said viral therapeutic agent comprises a localization signal component and a therapeutic agent component, wherein said therapeutic agent component is a nucleic acid, and wherein said localization signal component comprises a protein, comprising the steps of:*

(*1*) *preparing said viral therapeutic agent for administration by tethering said localization signal component to said therapeutic agent component; and*

(*2*) *administering said viral therapeutic agent to a cell in vitro, wherein said localization signal component causes said therapeutic agent component to be localized with said viral target in a cellular or viral compartment of said cell.*

6. A viral therapeutic agent comprising at least one localization signal *component and a therapeutic agent component, wherein said localization signal component is a protein that is* able to localize said *therapeutic* agent *component* in the same cellular or viral compartment with a viral target of said therapeutic agent *component* in a cell in vitro, *and wherein the therapeutic agent component is a nucleic acid*.

7. The *viral* therapeutic agent of claim 6, wherein said therapeutic agent *component* is selected from the group consisting of an antisense oligonucleotide, a decoy oligonucleotide and a ribozyme.

9. A therapeutic agent comprising a localization signal *component* and a therapeutic agent *component, wherein said therapeutic agent component is a nucleic acid, and* wherein said localization signal *component* is *a protein or non-viral nucleic acid* capable of localizing said therapeutic agent *component* in the same cellular compartment as the target molecule of said therapeutic agent *component in a cell in vitro*.

14. *A viral therapeutic agent comprising at least one localization signal component and a therapeutic agent component, wherein*

(*a*) *the localization signal component is able to localize said therapeutic agent component in the same cellular or viral compartment with a viral target of said therapeutic agent component in a cell in vitro,*

(*b*) *the therapeutic agent component is a nucleic acid, and*

(*c*) *the localization signal component is other than an HIV nucleic acid.*

15. *The viral therapeutic agent of claim 14, wherein said therapeutic agent component is selected from the group consisting of an antisense oligonucleotide, a decoy oligonucleotide and a ribozyme.*

16. *The viral therapeutic agent of claim 14, wherein said localization signal component comprises a protein.*

17. *The viral therapeutic agent of claim 6, wherein said therapeutic agent component is an inhibitory RNA.*

18. *The viral therapeutic agent of claim 17, wherein said inhibitory RNA is 19 nucleotides or 40 nucleotides in length.*

19. *The therapeutic agent of claim 9, wherein said therapeutic agent component is an inhibitory RNA.*

20. *The therapeutic agent of claim 19, wherein said inhibitory RNA is 19 nucleotides or 40 nucleotides in length.*

21. *The viral therapeutic agent of claim 14, wherein said therapeutic agent component is an inhibitory RNA.*

22. *The viral therapeutic agent of claim 21, wherein said inhibitory RNA is 19 nucleotides or 40 nucleotides in length.*

23. *The therapeutic agent of claim 9, wherein said localization signal component comprises a non-viral nucleic acid.*

24. *The therapeutic agent of claim 9, wherein said localization signal component comprises a protein.*

25. *A therapeutic agent comprising at least one localization signal component and a therapeutic agent component, wherein:*

(*a*) *the localization signal component is able to localize said therapeutic agent component in the same cellular compartment with a target of said therapeutic agent component in a cell in vitro,*

(*b*) *the therapeutic agent component is a nucleic acid, and*

(*c*) *the localization signal component is other than an HIV nucleic acid.*

26. *The therapeutic agent of claim 25, wherein said therapeutic agent component is selected from the group consisting of an antisense oligonucleotide, a decoy oligonucleotide and a ribozyme.*

27. *The therapeutic agent of claim 25, wherein said localization signal component comprises a protein.*

28. *The therapeutic agent of claim 25, wherein the therapeutic agent component is an inhibitory RNA.*

29. *The therapeutic agent of claim 28, wherein said inhibitory RNA is 19 nucleotides or 40 nucleotides in length.*

\* \* \* \* \*